ized Patent [19]

United States Patent [19]  
Podszun et al.

[11] 4,394,465  
[45] Jul. 19, 1983

[54] DENTAL MATERIALS BASED ON ORGANIC PLASTICS IN PASTE FORM

[75] Inventors: Wolfgang Podszun, Cologne; Michael Walkowiak, Leverkusen; Hans-Hermann Schulz, Leichlingen, all of Fed. Rep. of Germany

[73] Assignee: Bayer Aktiengesellschaft, Leverkusen, Fed. Rep. of Germany

[21] Appl. No.: 184,570

[22] Filed: Sep. 5, 1980

[30] Foreign Application Priority Data

Sep. 26, 1979 [DE] Fed. Rep. of Germany ....... 2938875

[51] Int. Cl.$^3$ .......................... A61K 6/08; C08K 3/36; C08K 3/40
[52] U.S. Cl. .................... 523/116; 523/214; 523/217; 523/220; 260/998.11; 524/494; 524/533; 525/254; 525/304; 525/305
[58] Field of Search .............. 260/42.15, 42.52, 42.53, 260/998.11, DIG. 36, 42.29; 525/254, 304, 305; 428/402; 523/116, 220, 217, 214

[56] References Cited

U.S. PATENT DOCUMENTS

| | | | |
|---|---|---|---|
| 3,073,795 | 1/1963 | Veuerka | 260/42.53 |
| 3,534,122 | 10/1970 | Cornell | 525/265 |
| 3,632,677 | 1/1972 | Petner et al. | 525/305 |
| 3,835,090 | 9/1974 | Gander et al. | 260/42.15 |
| 3,914,341 | 10/1975 | Kliment et al. | 260/31.6 |
| 3,926,906 | 12/1975 | Lee et al. | 260/42.15 |
| 4,089,763 | 5/1978 | Dart et al. | 260/42.15 |
| 4,115,479 | 9/1978 | Daidone | 525/193 |
| 4,134,930 | 1/1979 | Kubota | 525/305 |
| 4,150,485 | 4/1979 | Lee et al. | 260/42.28 |
| 4,220,582 | 9/1980 | Orlowski et al. | 260/42.29 |
| 4,267,097 | 5/1981 | Michl et al. | 260/42.29 |
| 4,277,536 | 7/1981 | Podszun et al. | 428/402 |

FOREIGN PATENT DOCUMENTS 14515 8/1980 European Pat. Off. .

OTHER PUBLICATIONS

Derwent Abst., 14705w/09 Lee Pharm. (DT2437378), Feb. 20, 1975.
Derwent Abst., 51165w/31 ETAB Dent (DT2403211), Jul. 24, 1975.
Derwent Abst., 60883c/35 Dentsply Int (EP14515), [Feb. 1, 1979 (US008507)], Public Date Aug. 20, 1980.
Derwent Abst., 38596c/22, May 28, 1980, EP11186 Bayer (DT-849280-Nov. 14, 1978), "Pearl Polymer Filler . . . ".
Derwent Abst. 41846c/24, Jun. 11, 1980, Bayer, (EP 11761).
Derwent Abst. 41631c/24, Jun. 4, 1980, DT 2850917, Bayer.
Derwent Abst. 41632c/24, Jun. 4, 1980, DT 2850918, Bayer.

*Primary Examiner*—Melvyn I. Marquis
*Assistant Examiner*—Herbert J. Lilling
*Attorney, Agent, or Firm*—Sprung, Horn, Kramer & Woods

[57] ABSTRACT

The invention provides dental materials in paste form consisting essentially of (a) 18 to 50% by weight of a polymerizable binder, (b) 20 to 65% by weight of a crosslinked bead polymer with an average particle size of 5 to 150 μm and (c) 5 to 45% by weight of glass beads with an average particle size of 5 to 80 μm. The pastes of the invention are outstandingly suitable as a dental filling material.

14 Claims, No Drawings

DENTAL MATERIALS BASED ON ORGANIC PLASTICS IN PASTE FORM

The present invention relates to novel organic plastics paste formulations for use in dentistry.

The use of plastic materials containing fillers as materials for artificial teeth, bridges, crowns and dental fillings is known. To prepare dental fillings, these materials are usually used in the form of formulations consisting of inorganic fillers, if appropriate organic polymers and polymerisable binders.

Because of their consistency and tackiness, the materials known hitherto have technological and clinical disadvantages.

The material is introduced into the cavity by wiping in, and in many cases the composition introduced is partly stripped from the wall of the cavity, after introduction into the cavity, due to adhesion to the filling instrument. This phenomenon cannot as a rule be detected by the dentist and thus leads to non-parietal incomplete fillings with the known disadvantages.

The increased tackiness of the filling materials known hitherto has a particularly adverse effect in the case of multi-surface cavities. Thus, as is known from the amalgam filling technique, perfect filling of the cavity is only possible if a filling material is introduced in portions. In this filling technique, small portions are first pressed parietally into the angles of the cavity, and only then is the cavity filled. A corresponding procedure is not possible with the plastic materials known hitherto.

Whilst in the case of single-surface fillings in the region of the anterior teeth the shape of the surface is achieved by applying matrix bands, the shaping of occlusal surfaces with materials which have a tacky consistency presents difficulties. Thus the areas of the masticating surfaces could be shaped only coarsely in the case of materials known hitherto. Shaping by rotating abrasive and polishing instruments was thus usually required after hardening. As is known, damage to the adjacent enamel areas is as a rule unavoidable during this process. The results of this are distortions in the relief of the occlusal plane, and in some cases occlusal disharmony.

Attempts have been made to produce the desired shape of the surface by producing a "carvable" consistency. However, this "carvable" property only results when a certain degree of polymerisation has already been achieved. If the filling material is worked in this state, the filling surface can crack open or tear and thus damage to the filling cannot be excluded. These cracks, produced by "carving", can be openings for microorganisms and for dyestuffs, with the known effects. Moreover, working of materials which are already partly polymerised can lead to interference with the polymerisation.

According to the invention there is provided a dental material which is based on organic plastics and is in paste form and consists of (a) 18 to 50, preferably 22 to 35%, by weight of a polymerisable binder, (b) 20 to 65, preferably 25 to 55% by weight of a crosslinked bead polymer with an average particle size of 5 to 100 $\mu$m, (c) blass beads and, optionally, (d) up to 30% by weight of an inorganic filler, with an average particle size of 1 m$\mu$ to 1$\mu$.

It has been found, surprisingly, that these pastes are outstandingly suitable as a dental filling material.

The materials according to the invention can be prepared in a consistency which makes processing as is customary in the amalgam filling technique possible, that is to say they can be pressed in and shaped.

Because the materials have a non-tacky, firm consistency which is suitable for pressing-in, it is possible to fill single-surface and multi-surface cavities parietally in several portions. The special property of the material means that there is no formation of layers when filling is effected in portions, that is to say the individual portions bond to one another homogenously.

After introduction of a particular portion into the cavity and the pressing-in or adapting thereof, this portion remains in position without changing its shape, that is to say it cannot even be deformed elastically.

Furthermore, because of the special consistency, the cavity can be filled using so-called amalgam guns without the filling material being pulled off again from the wall of the cavity or continuing to adhere to the nozzle of the gun.

The materials according to the invention exhibit a consistency which allows shaping by instruments and is already obtained immediately after the mixing process. This consistency makes it possible for the occlusal individual form of the masticating surface to be shaped, after filling the cavity, by means of suitable instruments, for example of plastic or of metal, such as are used in the amalgam filling technique.

The paste-like dental materials, according to the invention, based on organic plastics are transformed, by hardening, into solid substances which have a tooth-like appearance and possess the advantage that they can readily be polished.

To prepare the dental materials according to the invention the above-mentioned amounts in parts by weight of polymerisable binder, crosslinked bead polymer, glass beads, and, optionally, the fine-particled inorganic filler together with 0.01 to 5 parts by weight of starter additive(s), are mixed to form a paste.

Inhibitors or light stabilisers can be added to facilitate compounding the paste. For certain indications it can be appropriate also to add dyestuffs.

Suitable polymerisable binders are esters of methacrylic acid and monohydric and polyhydric alcohols, optionally mixed with other vinyl monomers. A content of methacrylic acid esters of over 80% by weight is particularly favourable. Especially preferred polymerisable binders consist of esters of methacrylic acid with two or more polymerisable double bond to the extent of at least 50% by weight.

Examples of suitable esters of methacrylic acid which may be mentioned are aliphatic and cycloaliphatic esters, such as methyl methacrylate, ethyl methacrylate and cyclohexyl methacrylate.

Esters which are very particularly suitable are, furthermore, those of polyhydric alchohols with a molecular weight of 190 to 10,000, in particular esters of di- and trihydric alcohols with a molecular weight in the range from 190 to 800, such as ethylene glycol dimethacrylate, triethylene glycol dimethacrylate, neopentylglycol dimethacrylate or trimethylolpropane trimethacrylate, and also urethane and ureido polymethacrylates, which are accessible by reacting hydroxyalkyl methacrylates or aminoalkyl methacrylates with polyisocyanates, for example the compound

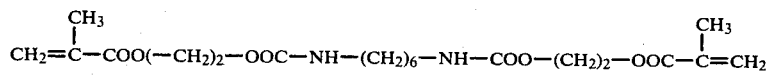

Very good pastes are obtained if at least a proportion of the binder used consists of compounds of the bis-GMA type, of the formula

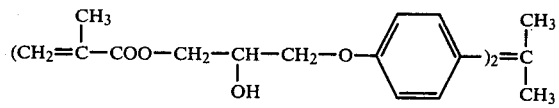

Dental filling compositions with a good consistency and a high level of mechanical strength are obtained, in particular, if mixtures of various methacrylic acid esters, for example mixtures of 20 to 70 parts by weight of bis-GMA and 80 to 30 parts by weight of triethylene glycol dimethacrylate, are used as the binder.

The crosslinked bead polymers employed to prepare the paste should preferably consist of polymerised methacrylic acid esters, especially methacrylic acid methyl ester, to the extent of more than 80% by weight. Of such crosslinked bead polymers, those which contain up to 50% of incorporated inorganic fillers with an average particle size of 1 m$\mu$ and 1$\mu$ are particularly preferred. Suitable monomers having a crosslinking action are polyvinyl compounds which can be copolymerised with methyl methacrylate, such as ethylene glycol dimethylacrylate or divinylbenzene, and the proportion of crosslinking agent should be 2 to 35% by weight of the monomer mixture. Besides the crosslinking agent, other monomers can be copolymerised in the bead polymer, for example in order to influence the swelling properties of the bead polymer or in order to modify the mechanical properties of the hardened dental plastic. The average particle size of the bead polymers employed should be between 5 and 100$\mu$; the range from 8 to 80$\mu$ is particularly favourable.

Bead polymers according to German Patent Applications P 28 49 280 of 14.11.78 and P 28 49 936 of 17.11.78 are also particularly suitable for the paste formulation. It is particularly advantageous to use bead polymers, containing inorganic fillers, according to P 28 49 936 of 17.11.78, since dental materials in which both the bead polymer and the interstices between the beads in the same way contain inorganic filler can be obtained in this manner.

The glass beads used should have an average bead diameter of 5 to 80$\mu$, preferably of 10 to 40$\mu$.

If it is important for the hardened dental material to be highly transparent, the refractive indices of the glass beads and of the polymer must be matched with one another. Glasses containing heavy metal ions, for example Ba, La or Zr, can be particularly advantageously employed for the preparation of a dental material which is opaque to X-rays.

Glass beads which are particularly suitable are, for example, "Reflexperlen" (Trade Mark) RPG 22 from Jenaer Glasswerke Schott und Gen./Mainz.

It is appropriate to silanise the glass beads, that is to say to treat them with a special adhesion-promoting silane compound (for example trimethoxy-(3-methacryloyloxypropyl)-silane or vinyltrimethoxy-silane) in order to improve the bond between the glass and the plastic matrix.

Suitable fine-particled inorganic fillers for the dental materials according to the invention are, above all, silicon dioxide, aluminium dioxide, silicates and silicate glasses, as long as their average particle size is in the range from 1 m$\mu$ to 1$\mu$. It is particularly advantageous to use amorphous silicon dioxide which has been obtained by flame pyrolysis, and in particular preferably amorphous silicon dioxide with a primary particle size of 5–30 m$\mu$ and a specific surface area, measured by the BET method, of 40–400 m$^2$/g.

The fine-particled inorganic filler can be silanised, like the glass beads, but this after-treatment step is not absolutely necessary for the preparation of the dental materials according to the invention.

The customary starter systems, that is to say systems which supply free radicals, anions or cations and which can trigger off free radical, anionic or cationic polymerisation, can be used to harden the dental materials according to the invention. Peroxides or aliphatic azo compounds, for example benzoyl peroxide, lauroyl peroxide or azoisobutyric acid dinitrile, are particularly suitable in the case of systems which supply free radicals, and are usually employed in amounts of 0.1 to 5% by weight. Whilst hardening at elevated temperature is carried out by peroxides or other free radical starters by themselves, it is necessary to add accelerators, preferably aromatic amines, for hardening at room temperature. Suitable accelerators are N,N-substituted toluidines and xylidines, such as N,N-dimethyl-p-toluidine or N,N-bis-(2-hydroxyethyl)-xylidine. Good hardening is achieved with an addition of 0.5–3% of amine. A favourable use form for a peroxide/accelerator activated system is the 2-paste form, one paste containing the free radical starter and the other containing the accelerator and hardening being initiated by mixing the two pastes.

Hardening using UV light or visible light with a suitable sensitisation is also a very good method. Examples of suitable photoinitiators are benzophenone and its derivatives, benzoin and its derivatives, such as benzoin ethers, anthraquinones and aromatic disulphides.

EXAMPLE 1

Preparation of a bead polymer filled with amorphous silicon dioxide

Polymerisation

Reaction vessel: 6 liter autoclave with a double-anchor stirrer

Solution I: 2,500 ml of distilled water

Dispersing agent solution: 500 ml of a 7.5% strength aqueous solution of the copolymer of 1 part by weight of methacrylic acid and 1 part by weight of methyl methacrylate, with a pH of 6 and a viscosity of 3,650 cp Solution II: 684 g of methyl methacrylate, 36 g of ethylene glycol dimethacrylate, 308 g of silanised amorphous silicon dioxide (surface area, measured by the BET method: 170 m$^2$/g) and 7.2 g of benzoyl peroxide.

Solution I is initially introduced into the autoclave and is stirred for 5 minutes. The stirrer is stopped, Solution II is added all at once and the autoclave is flushed with nitrogen. The pressure is then increased to 5 bars of nitrogen, the stirrer speed is adjusted to 400 rpm and the mixture is heated to 80° C. When the exothermic reaction started, the mixture is cooled to an extent such that the temperature remains below 90° C. The mixture is subsequently stirred at 80° C. for 2 hours.

Working-up

The mixture is let down and diluted to 10 liters with distilled water. After adding 180 g of glacial acetic acid, it is heated to 90° to 100° C. for 15 minutes. The bead polymer which precipitates is filtered off, after cooling, and is washed by being stirred three times in 5 liters of distilled water each time, and dried at 60° C. Yield: 866 g, average bead diameter: 45μ.

EXAMPLE 2

Paste-like dental material according to the invention (A) Peroxide paste 130 g of the bead polymer from Example 1, 100 g of Reflexperlen RPG 22 ®, 90 g of bis-GMA (Nupol 46–4005 from Messrs. Freeman Chemical), 50 g of triethylene glycol dimethacrylate and 2.5 g of benzoyl peroxide.

The individual components are introduced into a kneader and kneaded intensively for 60 minutes, a vacuum of about 20 mm Hg being applied during the last 10 minutes. A kneadable mass with a particularly firm consistency is obtained in this manner.

(B) Amine paste

The bead polymer, glass beads, bis-GMA and triethylene glycol dimethacrylate are employed and processed in the same amounts as in the case of the peroxide paste (A). However, instead of the peroxide, 1.8 g of N,N-dimethyltoluidine are employed.

(C) Paste-like composition for filling teeth

Equal parts (for example 200 mg each) of the amine paste and peroxide paste are mixed intensively for 30 seconds. The resulting mixture is outstandingly suitable as a dental filling material. It hardened in a few minutes with little shrinkage on polymerisation.

EXAMPLE 3

Paste-like dental material according to the invention

A paste-like mixture is prepared from 140 g of the bead polymer according to Example 1, 80 g of "Reflexperlen" RPG 22, 80 g of bis-GMA, 50 g of triethylene glycol dimethacrylate and 3 g of benzoin isopropyl ether, by a procedure corresponding to that indicated in Example 2.

This material is outstandingly suitable as a dental filling material. When irradiated with UV light (Uviolite lamp from Messrs. Espe), it hardens within 40 seconds in layer thicknesses of 2.5 mm.

What is claimed is:

1. A dental material which is based on organic plastics and is in paste form, characterized in that it comprises (a) 18 to 50% by weight of a polymerisable binder, (b) 20 to 65% by weight of a crosslinked bead polymer with an average particle size of 5 to 100 μm and (c) 5 to 45% by weight of glass beads with an average particle size of 5 to 80μ.

2. A dental material according to claim 1, characterized in that it consists essentially of (a) 22 to 35% by weight of the polymerisable binder, (b) 25 to 55% by weight of the crosslinked bead polymer and (c) 10 to 40% by weight of the glass beads.

3. A dental material according to claim 1 or 2, characterized in that it contains up to 30% by weight of an inorganic filler with an average particle size of 1 mμ to 1μ.

4. A dental material according to claims 1 or 2, characterized in that the polymerisable binder consists essentially of ester(s) of methacrylic acid to the extent of more than 80% by weight.

5. A dental material according to claim 4, characterized in that the polymerisable binder consists of ester(s) of methacrylic acid with two or more polymerizable double bonds to the extent of at least 50% by weight.

6. A dental material according to claims 1 or 2, characterized in that the crosslinked bead polymer has an average particle size of 8 to 80 μm.

7. A dental material according to claims 1 or 2, characterized in that the crosslinked bead polymer is build up from ester(s) of methacrylic acid to the extent of more than 80% by weight.

8. A dental material according to claim 7, characterized in that the crosslinked bead polymer contains up to 50% by weight of incorporated inorganic filler with an average particle size of 1 mμ to 1μ.

9. A dental material according to claim 1 or 2 characterized in that the glass beads have an average particle size of 10 to 40μ.

10. A dental material according to claims 1 or 2, characterized in that the glass beads are silanised.

11. A dental material according to claim 10, characterized in that the glass beads are treated with trimethoxy-(3-methylacryloyloxypropyl)-silane.

12. A dental material according to claim 10, characterized in that the glass beads are treated with vinyltrimethoxysilane.

13. A dental material according to claim 3, characterized in that the inorganic filler consists essentially of silicon dioxide.

14. A dental material according to claim 3, characterized in that the fine-particled inorganic fillers are silanized.

* * * * *